United States Patent [19]

Collins et al.

[11] 4,271,314

[45] Jun. 2, 1981

[54] 4,5-UNSATURATED PROSTANOIC ACID DERIVATIVES

[75] Inventors: Paul W. Collins, Deerfield; Raphael Pappo, Skokie, both of Ill.

[73] Assignee: G. D. Searle & Co., Skokie, Ill.

[21] Appl. No.: 98,290

[22] Filed: Nov. 28, 1979

[51] Int. Cl.³ .......................................... C07C 177/00
[52] U.S. Cl. ................................... 560/121; 562/503; 568/379; 424/305; 424/317; 424/331
[58] Field of Search ........................ 560/121; 562/503

[56] References Cited

U.S. PATENT DOCUMENTS 3,965,143  6/1976  Collins et al. .................... 560/121

*Primary Examiner*—Robert Gerstl
*Attorney, Agent, or Firm*—Albert Tockman

[57] ABSTRACT

4,5-Unsaturated 16-hydroxy prostanoic acid derivatives displaying valuable pharmacological properties, e.g. gastric antisecretory, are described herein.

7 Claims, No Drawings

4,5-UNSATURATED PROSTANOIC ACID DERIVATIVES

SUMMARY OF THE INVENTION

The present invention is concerned with novel 4,5-unsaturated 16-hydroxy prostanoic acid derivatives represented by the following structural formula

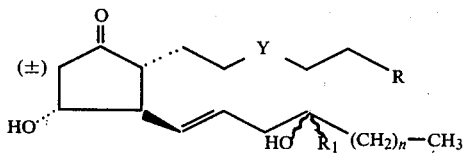

wherein R is —CH$_2$OH or —COOR', wherein R' is hydrogen or alkyl of 1–6 carbon atoms; R$_1$ is hydrogen or alkyl of 1–6 carbon atoms; n is an integer of from 2–4; Y is a cis-vinylene or trans-vinylene group; and the (+) refers to the compound shown, its mirror image and the mixture of racemates.

The lower alkyl radicals represented in the foregoing structural formula are typified by methyl, ethyl, propyl, butyl, pentyl, hexyl and the branched chain radicals thereof.

Also included in the invention are the individual stereoisomers, the mixture of isomers being represented by the wavy lines in the above formula.

Compounds of the present invention wherein Y is a cis-vinylene group can be represented by the following structural formula

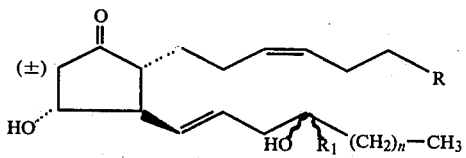

wherein R, R$_1$ and n are as defined above. Preferred compounds of this group are those wherein R is —COOR', wherein R' is hydrogen or alkyl of 1–6 carbon atoms. Particularly preferred compounds of this group are those compounds wherein n is 3.

Compounds of the present invention wherein Y is a trans-vinylene group can be represented by the following structural formula

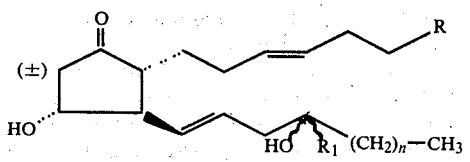

wherein R, R$_1$ and n are as defined above.

DETAILED DESCRIPTION OF THE INVENTION

The novel compounds of the present invention display valuable pharmacological properties as is exemplified by their ability to inhibit the gastric secretion stimulated by secretogogues such as histamine and pentagastrin while furthermore possessing the surprising advantage of lacking the potent undesirable side-effects displayed by related substances.

The specific assay used to detect gastric antisecretory activity is described as follows.

Adult female beagle dogs weighing 13—20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

Starting materials suitable for the manufacture of the compounds of the present invention are the cyclopent-1-enealkanoic acids and esters of the following formula

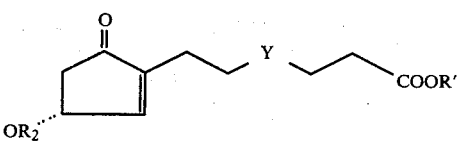

wherein Y and R' are as defined hereinbefore and R$_2$ is a protecting group such as tri(lower alkyl)silyl, tetrahydrofuranyl or tetrahydropyranyl. The manufacture of these starting materials are described in Examples 1–12 and is outlined in the following scheme:

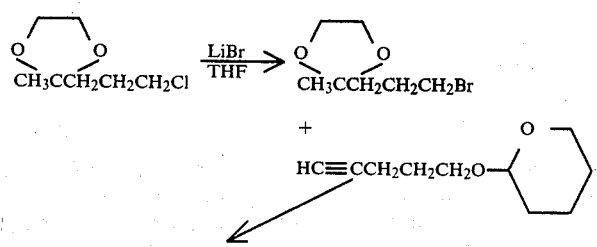

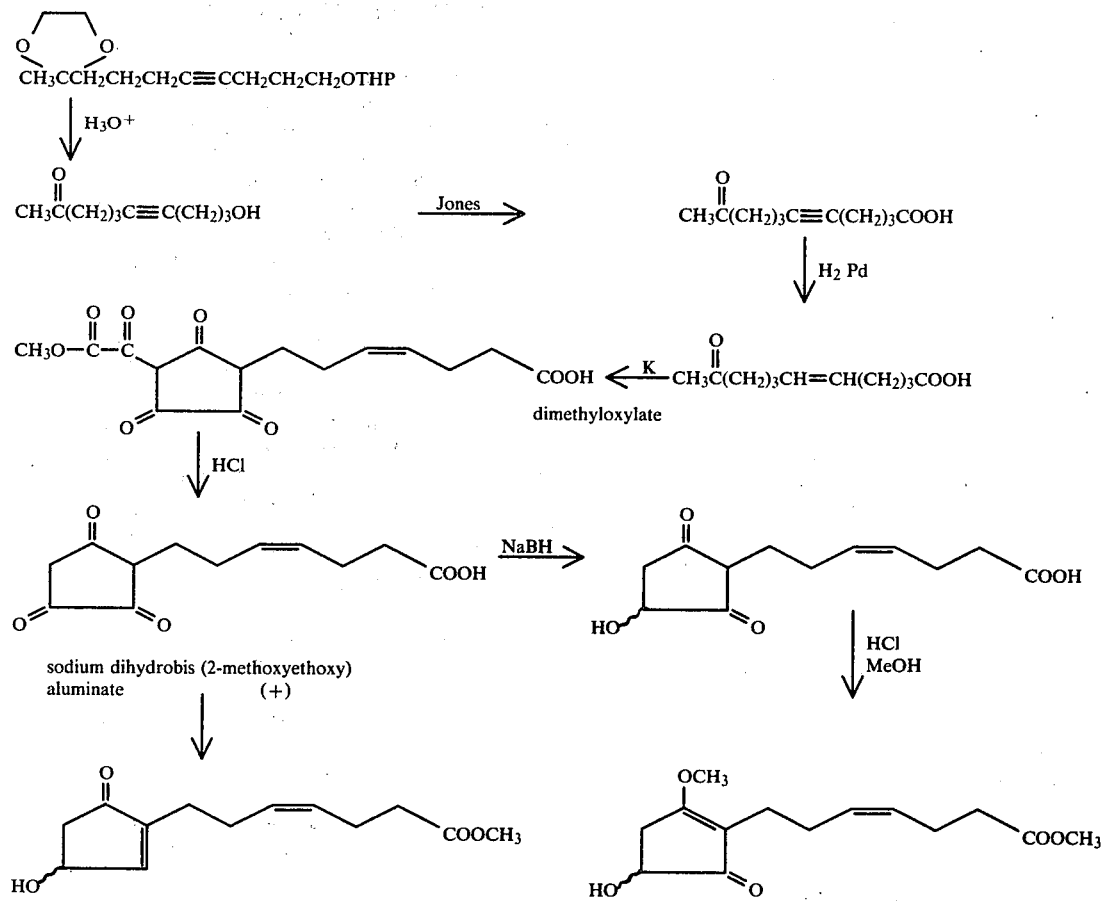

Introduction of the oxygenated trans-vinyl side chain at the 2-position of the cyclopentane ring is effected by reaction with a suitable organometallic reagent. The oxygenated trans-vinyl side chain groups are manufactured from the corresponding acetylenes by the process described by Pappo et al in *Chemistry, Biochemistry, and Pharmacological Activity of Prostanoids*, 17–26 (1979). Example 13 describes the manufacture of a trans-vinylstannane starting material from the corresponding acetylene. After the side chain is introduced, the oxygen protecting groups are conveniently removed with a weak acid solution such as acetic acid.

The compounds wherein R is a hydroxymethyl group are manufactured from the enol ether of the corresponding ester as exemplified in Example 17 and 18. The protected prostanoic ester produced by the reaction of the starting materials is treated with triethyloxonium tetrafluoroborate to produce the corresponding enol ether. The enol ether is reduced with lithium aluminum hydride and acidified with a weak acid to afford the corresponding 9-oxo-11,16-dihydroxyprost-4,13-dien-1-ol.

When a resolved side chain is substituted for the racemic side chain there is formed a mixture of diastereoisomers (Examples 20 and 21). This mixture of diastereoisomers may then be chromatographed to afford the individual stereoisomeric products (Example 22).

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (°C.) and quantities of materials in parts by weight unless otherwise noted.

EXAMPLE 1

4.0 Parts of 5-chloro-2-pentanone ethylene ketal is mixed with 9.0 parts of lithium bromide and 2.0 parts of diisopropylethylamine in 30 parts by volume of tetrahydrofuran which has been distilled from lithium aluminum hydride. The mixture is refluxed under nitrogen for 48 hours, cooled and poured into a mixture of ether and water for extraction. The ether layer is washed twice with water, then with 1 N hydrochloric acid and then twice again with water. The ether layer is then dried over sodium sulfate and evaporated under reduced pressure to give 5-bromo-2-pentanone ethylene ketal having the formula

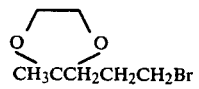

EXAMPLE 2

0.1 Part of p-toluenesulfonic acid is added to a stirred mixture of 4.2 parts 4-pentyn-1-ol and 5.0 parts dihydropyran. After about 30 minutes, the mixture is treated with 0.5 part of triethylamine and vacuum distilled to give 2-tetrahydropyranyl-4-pentynyl ether having the formula

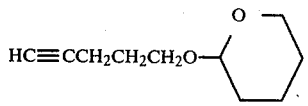

EXAMPLE 3

A solution containing 18.5 parts of 2-tetrahydropyranyl-4-pentynyl ether of Example 2 in 125 parts by volume of tetrahydrofuran which has been freshly distilled from lithium aluminum hydride is cooled to approximately −30° C. and treated with 46 parts by volume of 2.4 molar n-butyl lithium solution in hexane. The solution is allowed to come to room temperature. After approximately 30 minutes at room temperature, 21 parts of 5-bromo-2-pentanone ethylene ketal of Example 1 is added, followed by the addition of 30 parts by volume of hexamethylphosphoric triamide, with stirring. After 1 hour the reaction mixture is poured into a mixture of ether and 1 N hydrochloric acid. The ether layer is washed with water, dried over sodium sulfate and stripped of solvent in vacuo to give, as a colorless, viscous liquid, the product having the formula

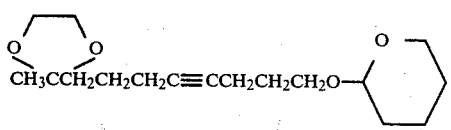

EXAMPLE 4

30 Parts of the decynyl ketal of Example 3 is dissolved in a mixture of 150 parts by volume of 1 N hydrochloric acid, 200 parts by volume of tetrahydrofuran and 50 parts by volume of methanol. The solution is maintained at room temperature for 48 hours and then refluxed for 5–6 hours. The solution is then cooled to room temperature and solid potassium carbonate is added until the pH reaches 7. The solution is then stripped to ⅛ of its volume, diluted with water and extracted with ether twice. The ether extracts are combined, washed with water, dried over sodium sulfate and stripped of solvent to give 9-oxodec-4-yn-1-ol which is used without purification in Example 5.

EXAMPLE 5

20 Parts of 9-oxodec-4-yn-1-ol of Example 4 is dissolved in 200 parts by volume of acetone and cooled to 0° C. The cold solution is stirred and treated dropwise with 90 parts by volume of 2.67 molar Jones reagent (chromic acid in sulfuric acid and water). The acetone solution is decanted from the solid chromium salts, which are then rinsed with fresh acetone. The acetone solutions are combined and poured into a mixture of ether and water. The ether layer is separated from the water, washed once with water, and then extracted three times with 5% potassium carbonate solution. The alkaline extracts are combined, acidified with concentrated hydrochloric acid and extracted twice with ether and once with ethyl acetate. The extracts are combined, dried over sodium sulfate, and stripped of solvent to give the pure product, 9-oxodec-4-ynoic acid.

EXAMPLE 6

10 Parts of the 9-oxodec-4-ynoic acid of Example 5 is hydrogenated at room temperature in toluene containing about 0.5% quinoline with 5% palladium on barium sulfate as catalyst. The toluene solution is washed with 1 N hydrochloric acid, then water. The solution is dried over sodium sulfate and stripped of solvent to give, as a yellow oil, the product cis-9-oxodec-4-enoic acid.

EXAMPLE 7

3.2 Parts of potassium metal is added to 50 parts by volume of t-butyl alcohol and refluxed under argon. After the potassium has dissolved, a solution of 2.52 parts of cis-9-oxodec-4-enoic acid and 4.85 parts of dimethyloxalate, which has been recrystallized from hexane in 25 parts by volume of t-butyl alcohol is added dropwise to the refluxing solution over a one hour period. The reaction mixture is refluxed for 2 hours more, cooled to room temperature and filtered under argon. The orange filter cake is added to a mixture of chloroform and 1 N hydrochloric acid. The chloroform layer is washed with a saturated sodium chloride solution, dried over sodium sulfate and stripped of solvent to give the product 7-(2,3,5-trioxo-4-methoxalylcyclopentane)-hept-4-cis-enoic acid having the formula

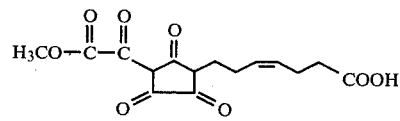

and its various tautomeric enol forms.

EXAMPLE 8

4.0 Parts of the 7-(2,3,5-trioxo-4-methoxyalylcyclopentane)hept-4-cis-enoic acid of Example 7 is added to 100 parts by volume of 1 N hydrochloric acid and refluxed under argon for 3 hours. The solution is cooled to room temperature, filtered and extracted twice with ethyl acetate. The extracts were combined and washed twice with saturated sodium chloride solution, dried and stripped of solvent to give a red oil. The red oil is chromatographed on silica gel (60% ethyl acetate, 39% hexane and 1% acetic acid as eluent) to give 7-(2,3,5-trioxocyclopentane)hept-4-cis-enoic acid as a yellow solid melting at 78°–80° C. and having the formula

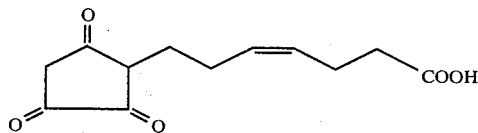

and its various tautomeric enol forms.

EXAMPLE 9

1.15 Parts of 7-(2,3,5-trioxocyclopentane)hept-4-cis-enoic acid is dissolved in 35 parts by volume of ethanol and 30 parts by volume of water and cooled to 0° C. 0.55 Part of sodium borohydride is dissolved in 5.0 parts by volume of water and added dropwise to the ethanol solution. After the addition is complete, the solution is stirred at 0° C. for 30 minutes. The solution is poured into ethyl acetate and 1 N hydrochloric acid. The aqueous layer is extracted three times with additional ethyl acetate. The ethyl acetate extracts are combined, washed once with saturated sodium chloride, dried over sodium sulfate and stripped of solvent to give, as a viscous yellow oil, (+)7-(2,5-dioxo-3-hydroxycyclopentane)hept-4-cis-enoic acid having the formula

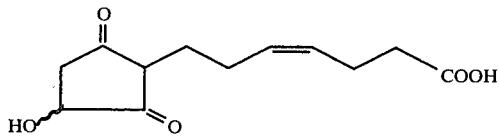

and its various tautomeric enol forms.

EXAMPLE 10

To a solution of 2.0 parts of (+)7-(2,5-dioxo-3-hydroxycyclopentane)hept-4-cis-enoic acid in 30 parts by volume of dry methanol is added 10 parts by volume of 2,2-dimethoxypropane and 4 parts by volume of 1% methanolic hydrochloride. The mixture is allowed to stand at room temperature for 48 hours and is then stripped to dryness at room temperature under reduced pressure. About 4 parts by volume of ether is added and the mixture is allowed to stand at room temperature for an additional 48 hours. The solidified mixture is taken up in toluene containing 1% triethylamine, and the solution is washed successively with dilute potassium carbonate and water, dried over sodium sulfate and stripped of solvent. The residue is recrystallized from ether to give, as a white solid melting at 82°–84° C., the product (+)methyl 7-(4-hydroxy-2-methoxy-5-oxocyclopent-1-ene)hept-4-cis-enoate, having the formula

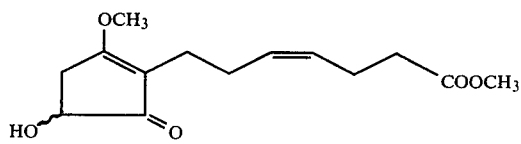

EXAMPLE 11

100 Parts by volume of dry toluene are placed in a three-neck flask and cooled to −70° C. in an isopropyl alcohol-dry ice bath. In separate dropping funnels are placed 15.5 parts by volume of 1.83 molar sodium dihydrobis-(2-methoxyethoxy)aluminate diluted with 100 parts by volume of toluene and a solution of 6.92 parts of (+)methyl 7-(4-hydroxy-2-methoxy-5-oxocyclopent-1-ene)hept-4-cis-enoate in 200 parts by volume of toluene. The two solutions are added dropwise and simultaneously to the flask. The temperature of the flask should not be allowed to exceed −60° C. during the additions. The mixture is stirred at −70° C. for 3.5 hours and then at 0° C. for 15 minutes, quenched with a solution of 5.0 parts by volume methanol in 10 parts by volume of toluene, and acidified with 150 parts by volume of 1 N hydrochloric acid. The organic layer is separated, washed with water, dried over sodium sulfate and stripped of solvent. The residue is chromatographed on silica gel (70% ethyl acetate, 30% hexane as eluent) to give, as a viscous oil, (+)methyl 7-(3-hydroxy-5-oxocyclopent-1-ene)hept-4-cis-enoate having the formula

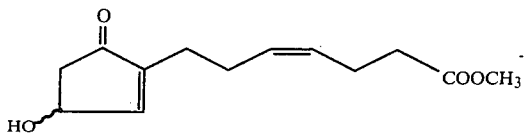

EXAMPLE 12

2.6 Parts of (+)methyl 7-(3-hydroxy-5-oxocyclopent-1-ene)hept-4-cis-enoate is dissolved in 20 parts by volume of dimethylformamide and treated successively with 1.0 part of imidazole and 1.9 parts of triethylsilyl chloride. The solution is stirred for 1 hour at room temperature, diluted with ether, washed with water 3 to 4 times, dried over sodium sulfate and stripped of solvent. The product, which is used directly in Example 14 is (+)methyl 7-(3-triethylsilyloxy-5-oxocyclopent-1-ene)hept-4-cis-enoate having the formula

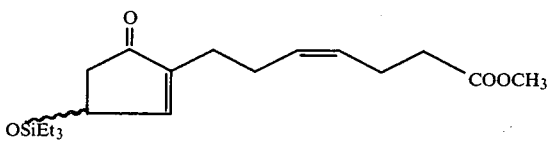

EXAMPLE 13

2.12 Part of 4(RS)-trimethylsiloxy-4-methyl-1-octyne and 3.0 parts of tri-n-butyltin hydride are mixed and irradiated under argon with a sunlamp at 0° C. for 2 hours and then at 55° C. for 2 hours. The resulting product is used directly in Example 14.

EXAMPLE 14

1.0 Part of the trans-vinylstannane product of Example 13 is dissolved in 3.0 parts by volume of dry tetrahydrofuran, cooled to −60° C. and treated with 0.87 part by volume of a 2.3 molar solution of n-butyllithium in hexane. The solution is stirred for an hour at −60° C. and then treated with an ether solution containing 0.26 part of copper 1-pentynylide and 0.64 part of hexamethylphosphorous triamide. The solution is then stirred for an additional 10 minutes at −60° C. and an ether solution containing 0.35 part of the (+)methyl 7-(3-triethylsilyloxy-5-oxocyclopent-1-ene)hept-4-cis-enoate of Example 12 is added. The solution is stirred for one hour and poured into a mixture of ether and 1 N hydrochloric acid. The ether layer was separated, washed with water twice, filtered, dried over sodium sulfate and stripped of solvent. The residue is chromatographed on silica gel (10% ethyl acetate, 90% hexane as eluent) to give the product racemic methyl 7-[3α-triethylsilyloxy-2β-(4(RS)-4-trimethylsilyloxy-4-methyl-1-trans-octenyl)-5-oxocyclopentane]-1α-hept-4-cis-enoate having the formula

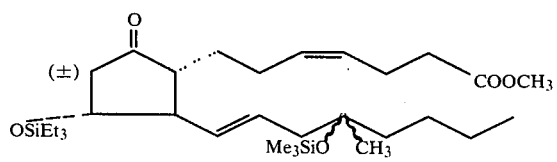

EXAMPLE 15

0.30 Part of methyl 7-[3α-triethylsilyloxy-2β-(4(RS)-4-trimethylsilyloxy-4-methyl-1-trans-octenyl)-5-oxocyclopentane]-1α-hept-4-cis-enoate is dissolved in 5.0 parts by volume of a 3:1:1 mixture of acetic acid:tetrahydrofuran:water and is allowed to stand at room temperature for about 30 minutes. The solution is diluted with ether, washed with water 5 times, dried over sodium sulfate and stripped of solvent. The residue is chromatographed on silica gel (100% ethyl acetate as eluent) to give, as a viscous colorless oil, the product racemic methyl 7-[3α-hydroxy-2β-(4(RS)-4-hydroxy-4-methyl-1-trans-octenyl)-5-oxocyclopentane]-1α-hept-4-cis-enoate having the formula

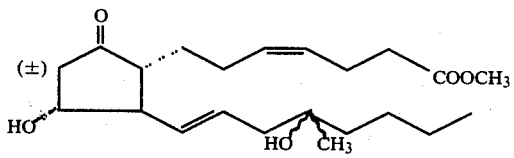

EXAMPLE 16

1.0 Part of racemic methyl 7-[3α-hydroxy-2β-(4(RS)-4-hydroxy-4-methyl-1-trans-octenyl)-5-oxocyclopentane]-1α-hept-4-cis-enoate is dissolved in 50 parts by volume of 95% ethanol and added to 300 parts by volume of a 7.8 pH TRIS(2-amino-2-hydroxymethyl-1,3-propanediol) buffer. This mixture is treated with 0.15 part of hog liver esterase (Sigma Chemical Co. No. E-3128) and stirred for 3 to 4 hours at room temperature. The mixture is diluted with ether, washed with 1 N hydrochloric acid, then water, dried over sodium sulfate and stripped of solvent. The residue is chromatographed on silica gel (100% ethyl acetate as eluent) to give the product racemic 7-[3α-hydroxy-2β-(4(RS)-4-hydroxy-4-methyl-1-trans-octenyl)-5-oxocyclopentane]-1α-hept-4-cis-enoic acid having the formula

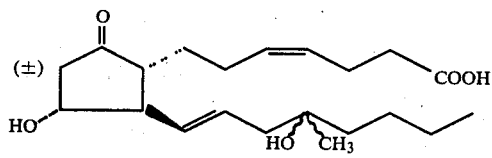

EXAMPLE 17

1.0 Part of the trans-vinylstannane product of Example 13 is dissolved in 3.0 parts by volume of dry tetrahydrofuran, cooled to −60° C. and treated with 0.87 parts by volume of a 2.3 molar solution of n-butyllithium in hexane. The reaction is stirred for one hour at −60° C. and then treated with an ether solution containing 0.26 part of copper 1-pentynilide and 0.64 part of hexamethylphosphorous triamide. The solution is then stirred for an additional 10 minutes at −60° C. and an ether solution containing 0.35 part of the (+)methyl 7-(3-triethylsilyloxy-5-oxocyclopentane)hept-4-cis-enoate of Example 12 is added. The solution is stirred for one hour and then treated with 3.0 parts by volume of triethyloxonium tetrafluoroborate (1 molar in methylene chloride). The mixture is stirred at −50° C. for 30 minutes and then allowed to come slowly up to 0° C. The mixture is then poured into ether and dilute potassium bicarbonate solution. The layers are separated and the ether layer is washed with additional dilute potassium bicarbonate solution, dried over sodium sulfate and stripped of solvent. The residue is chromatographed on silica gel (10% ethyl acetate, 90% hexane with 0.2% triethylamine as eluent) to give racemic methyl 7-[3-triethylsilyloxy-2β-(4(RS)-4-trimethylsilyloxy-4-methyl-1-trans-octenyl)-5-ethyloxycyclopent-1(5)-ene]-1α-hept-4-cis-enoate having the formula

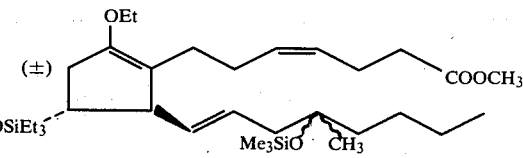

EXAMPLE 18

2.0 Parts of racemic methyl 7-[3-triethylsilyloxy-2β-(4(RS)-4-trimethylsilyloxy-4-methyl-1-trans-octenyl)-5-ethyloxycyclopent-1(5)-ene]-1α-hept-4-cis-enoate is dissolved in 100 parts by volume of dry tetrahydrofuran, cooled to 0° C. and treated with 0.3 part of lithium aluminum hydride. After 15 minutes at 0° C., the reaction mixture is poured into ether and water. The ether layer is separated, washed again with water, dried over sodium sulfate and stripped of solvent. The residue is taken up in 50 parts by volume of a 3:1:1 mixture of acetic acid, water and tetrahydrofuran and is allowed to stand at room temperature for 30 minutes. The solution is diluted with ether washed with water 4 to 5 times, dried over sodium sulfate and stripped of solvent. The residue is chromatographed on silica gel (100% ethyl acetate as eluent) to give, as a colorless viscous oil, the product racemic 7-[3α-hydroxy-2β-(4(RS)-4-hydroxy-4-methyl-1-trans-octenyl)-5-oxocyclopentane]-1α-hept-4-cis-en-1-ol having the formula

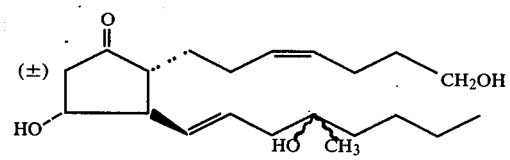

EXAMPLE 19

The $\Delta^{4,5}$ trans prostanoic acid derivatives of the present invention are prepared by the following procedures:

0.10 Part of lithium metal is added to 15 parts by volume of anhydrous ammonia in a 3-necked flask fitted with a dry ice condenser and immersed in a dry ice-isopropanol bath. 1.5 Parts of the product of Example 3 and 0.5 part by volume of t-butanol are mixed and added dropwise to the ammonia solution. The reaction mixture is stirred for 2 hours after the addition is complete. The flask is removed from the ice bath and the reaction mixture is quenched with solid ammonium chloride. Ether is then added dropwise allowing the ammonia to evaporate. The solution is poured into ether and dilute hydrochloric acid. The ether layer is separated, washed twice with dilute hydrochloric acid, then water, dried over sodium sulfate and stripped of solvent to give the product having the formula

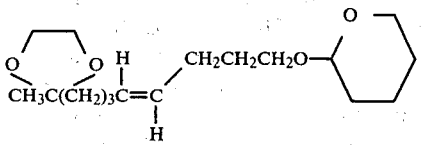

When the above trans compound is substituted for the acetylene compound of Example 4 and carried through Examples 5,7,8,9,10,11,12,14 and 15 there is obtained the product racemic methyl 7-[3α-hydroxy-2β-(4(RS)-4-hydroxy-4-methyl-1-trans-octenyl)-5-oxocyclopentane)-1α-hept-4-trans-enoate having the formula

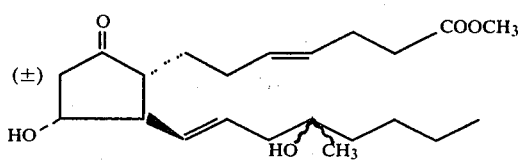

When the above ester is substituted in Example 16 there is obtained the product racemic 7-[3α-hydroxy-2β--(4(RS)-4-hydroxy-4-methyl-1-trans-octenyl)-5-oxocyclopentane]-1α-hept-4-trans-enoic acid having the formula

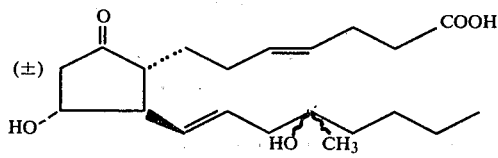

When the trans starting material above is substituted for the acetylene compound in Example 4 and carried through Examples 5,7,8,9,10,11,12,17 and 18 there is obtained the product racemic 7-[3α-hydroxy-2β-(4(RS)-4-hydroxy-4-methyl-1-trans-octenyl)-5-oxocyclopentane]-1α-hept-4-trans-en-1-ol having the formula

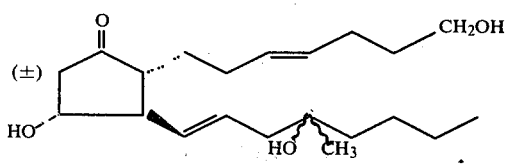

EXAMPLE 20

2.12 Parts of (4S)-4-trimethylsilyloxy-4-methyl-1-octyne which was obtained by the method described in "Recent Developments in the Synthesis of Antisecretory Prostaglandins", R. Pappo et al in *Chemistry, Biochemistry and Pharmacological Activity of Prostanoids*, 1979 and 3.0 parts of tri-n-butyltin hydride are mixed and irradiated under argon with a sunlamp at 0° C. for 2 hours and then at 55° C. for 2 hours. The resulting product is used directly in Example 21.

EXAMPLE 21

1.0 Part of the trans-vinylstannane product of Example 20 is dissolved in 3.0 parts of volume of dry tetrahydrofuran, cooled to −60° C. and treated with 0.87 part by volume of a 2.3 molar solution of n-butyllithium in hexane. The solution is stirred for an hour at −60° C. and then treated with an ether solution containing 0.26 part of copper 1-pentynylide and 0.64 part of hexamethylphosphorous triamide. The solution is then stirred for an additional 10 minutes at −60° C. and an ether solution containing 0.35 part of the racemic methyl 7-(3-triethylsilyloxy-5-oxocyclopent-1-ene)hept-4-cis-enoate of Example 12 is added. The solution is stirred and poured into a mixture of ether and 1 N hydrochloric acid. The ether layer was separated, washed with water twice, filtered, dried over sodium sulfate and stripped of solvent. The residue is chromatographed on silica gel (10% ethyl acetate, 90% hexane as eluent) to give a mixture of diastereoisomers methyl 7-[3(S)-triethylsilyloxy-2β-(4(S)-trimethylsilyloxy-4-methyl-1-trans-octenyl)-5-oxocyclopentane]-1α-hept-4-cis-enoate having the formula

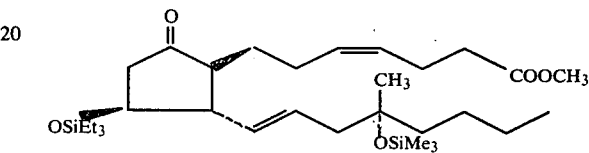

and methyl 7-[3-(R)-triethylsilyloxy-2β-(4(S)-trimethylsilyloxy-4-methyl-1-trans-octenyl)-5-oxocyclopentane]-1α-hept-4-cis-enoate having the formula

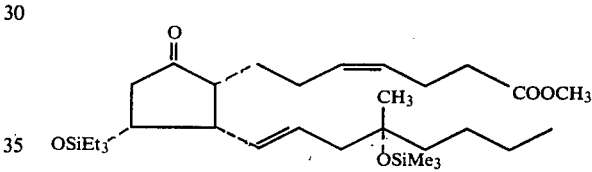

EXAMPLE 22

0.30 Part of the diastereoisomers of Example 21 is dissolved in 5.0 parts by volume of a 3:1:1 mixture of acetic acid:tetrahydrofuran:water and is allowed to stand at room temperature for about 30 minutes. The solution is diluted with ether, washed with water 5 times, dried over sodium sulfate and stripped of solvent. The residue is chromatographed on hydroxyapatite (6% n-butanol, 94% cyclohexane as eluent) to give the products methyl 7-[3(S)-hydroxy-2β-(4(S)-hydroxy-4-methyl-1-trans-octenyl)-5-oxocyclopentane]-1α-hept-4-cis-enoate followed by methyl 7-[3(R)-hydroxy-2β-(4(S)-hydroxy-4-methyl-1-trans-octenyl)-5-oxocyclopentane]-1α-hept-4-cis-enoate.

EXAMPLE 23

0.365 Part of racemic 7-[3(α)-hydroxy-2β-(4(RS)-4-hydroxy-4-methyl-1-trans-octenyl)-5-oxocyclopentane]-1α-hept-4-cis-enoic acid of Example 16 is dissolved in 5.0 parts by volume of dimethylsulfoxide and treated with 1.0 part isopropyl iodide and 0.35 part of N,N-diisopropylethylamine. The solution is stirred overnight. The solution is diluted with ether, washed with cold dilute hydrochloric acid and then 2-3 times with water, dried and chromatographed on silica gel (100% ethyl acetate as eluent) to give the product racemic isopropyl 7-[3(α)-hydroxy-2β-(4(RS)-4-hydroxy-4-methyl-1-trans-octenyl)-5-oxocyclopentane]-1α-hept-4-cis-enoate having the formula

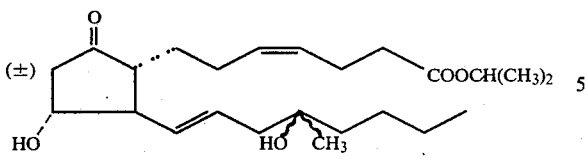

What is claimed is:
1. A compound of the formula

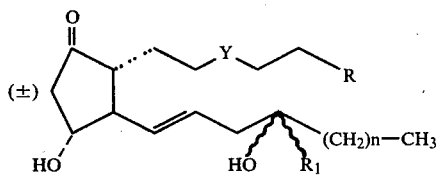

wherein R is

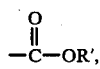

wherein R' is hydrogen or alkyl of 1–6 carbon atoms; $R_1$ is hydrogen or alkyl of 1–6 carbon atoms; n is an integer of from 2 through 4; Y is a cis-vinylene or trans-vinylene group; and the (±) refers to the compound shown, its mirror image and the mixture of racemates.

2. The compound according to claim 1 which is racemic 7-[3-hydroxy-2-(4(RS)-hydroxy-1-trans-octenyl)-5-oxocyclopentane]-1-hept-4-cis-enoic acid.

3. The compound according to claim 1 of the formula

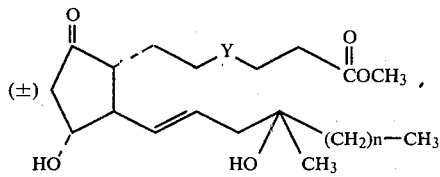

wherein n is an integer of from 2 through 4 and Y is a cis-vinylene or trans-vinylene group.

4. The compound according to claim 1 which is racemic methyl 7-[3-hydroxy-2-(4(RS)-hydroxy-4-methyl-1-trans-octenyl)-5-oxocyclopentane]-1-hept-4-cis-enoate.

5. The compound according to claim 1 which is racemic methyl 7-[3-hydroxy-2-(4(RS)-hydroxy-4-methyl-1-trans-oxtenyl)-5-oxocyclopentane]-1-hept-4-trans-enoate.

6. The compound according to claim 1 which is methyl 7-[3(S)-hydroxy-2-(4(S)-hydroxy-4-methyl-1-trans-octenyl)-5-oxocyclopentane]-1-hept-4-cis-enoate.

7. The compound according to claim 1 which is methyl 7-[3(R)-hydroxy-2-(4(S)-hydroxy-4-methyl-1-trans-ctenyl)-5-oxocyclopentane]-1-hept-4-cis-enoate.

* * * * *